United States Patent [19]
Yui et al.

[11] Patent Number: 5,876,451
[45] Date of Patent: Mar. 2, 1999

[54] MEDICAL DEVICE AND METHOD FOR PRODUCING THE SAME

[75] Inventors: Tooru Yui, Fujisawa; Tokuzo Nakagawa, Kamakura; Kazuo Kondo, Tokorozawa, all of Japan

[73] Assignees: Toyo Boseki Kabushiki Kaisha, Osaka; Bio-Engineering Laboratories, Ltd., Tokyo, both of Japan

[21] Appl. No.: 3,659

[22] Filed: Jan. 7, 1998

Related U.S. Application Data

[62] Division of Ser. No. 623,976, Mar. 29, 1996, Pat. No. 5,723,010.

[30]    Foreign Application Priority Data

Mar. 31, 1995  [JP]  Japan ..................................... 7-75914
Mar. 31, 1995  [JP]  Japan ..................................... 7-75915

[51] Int. Cl.$^6$ .................................. A61F 2/10; A61F 2/02
[52] U.S. Cl. ................................................ 623/15; 623/11
[58] Field of Search ........................................ 623/11, 15

[56]    References Cited

U.S. PATENT DOCUMENTS

| | | | |
|---|---|---|---|
| 4,361,552 | 11/1982 | Baur, Jr. .................................... | 424/582 |
| 5,275,826 | 1/1994 | Badylak et al. ......................... | 424/551 |
| 5,468,253 | 11/1995 | Bezwada et al. ....................... | 606/230 |

*Primary Examiner*—Mary Beth Jones
*Assistant Examiner*—John M. Black
*Attorney, Agent, or Firm*—Leydig, Voit & Mayer, Ltd.

[57]    ABSTRACT

A medical device having stratum compactum of tissue membrane is provided. The present invention further provides a method for producing a medical device having stratum compactum of tissue membrane. The method includes the steps of: separating tissue membrane including stratum compactum from tissue; sterilizing or disinfecting the separated tissue membrane; and removing all other layers except the stratum compactum from the sterilized or disinfected tissue membrane using an enzyme.

6 Claims, 5 Drawing Sheets

MEDICAL DEVICE AND METHOD FOR PRODUCING THE SAME

CROSS-REFERENCE TO RELATED APPLICATION

This application is a divisional of application Ser. No. 08/623,976, filed 29 Mar. 1996, now U.S. Pat. No. 5,723,010.

BACKGROUND OF THE INVENTION

1. Field of the Invention

The present invention relates to a medical device. More particularly, the present invention relates to a medical device used for a medical prosthesis and an artificial tissue which are implantable and tissue-regenerative, such as a pledget, a bolster, a patch graft, a suture,-wound and burn dressings, a donor-site skin graft, a post-operative antiadhesive, an artificial blood vessel, an artificial urethra, an artificial ureter, an artificial esophagus, an artificial trachea, an artificial membrana tympani, and an artificial oral mucosa.

2. Description of the Related Art

In the field of surgery, when damage, abnormality, dysfunction or the like occurs in a certain site of body tissue, the defective tissue is conventionally and frequently repaired by anaplerosis and prosthesis using an artificial substance as a medical device substituting the function of the tissue, for curing the tissue, preventing adhesion of the tissue and restricting the abnormal development of the tissue. The above-mentioned medical devices are required to have: biocompatibility in blood, biological fluid and/or body tissue; physical properties such as strength, elongation, softness and flexibility, and chemical and biological safety necessary for the portion and condition to be applied and suture and anastomosis; and suitable operativeness.

Generally, existing tissue-derived materials, whether homologous or heterologous, are conventionally used because of their acceptable safety and efficacy characteristics, even though undesirable conditions such as immunological rejection, blood coagulation, tissue hypertrophy, keloid or the like may be caused in some cases when enthesis is conducted. The tissue-derived materials include medical devices derived, for example, from human cerebral dura mater, human fascia lata, horse pericardium and pig pericardium.

On the other hand, synthetic polymer materials are also widely used as medical devices because such materials have excellent physical properties which can be easily controlled. However, many of the synthetic polymer materials are inferior to the aforementioned tissue-derived materials in terms of biocompatibility, bioaffinity and the like. Moreover, these synthetic polymer materials lack physiological function, for example, tissue regeneration. Therefore, the synthetic polymer materials merely substitute the body tissue with foreign substances. Thus, a novel medical device possessing the above-mentioned excellent characteristics is still required.

As medical devices made of such tissue-derived materials or synthetic polymer materials, the following materials have been conventionally developed.

For examples Japanese Patent Publication No. 3-4229 relates to a medical prosthesis utilizing human amnion. U.S. Pat. No. 4,361,552 relates to a burn dressing in which a crosslinked human amnion is used.

Furthermore, Japanese Patent Publication No. 58-52662 relates to a structure for covering damage made of an air permeable cloth substrate on which collagen-dispersed gel is carried. Japanese National Publication No. 61-502129 relates to a collagen-based biodegradable matrix for use in the topical application of an external or internal wound.

However, none of the above-mentioned medical devices described in the publications sufficiently satisfies all of the above required properties. The above-mentioned medical devices satisfy only a specific property among biocompatibility, strength, flexibility, operativeness for operation, but they do not satisfy the other properties such as biocompatibility, strength, flexibility and operativeness. Otherwise, even though some of the above-mentioned medical devices may possess all properties to a certain level, the levels are insufficient for each of the required properties.

More specifically, for example, human amnion described in Japanese Laid-Open Patent Publication No. 3-4229 comprises cells and cytoplasm such as an epithelium layer and a fibroblast layer. Therefore, there is a possibility that serious side-effects are caused due to the activity of a slow virus, the activity of prion which is a pathogen causing Creutzfeldt-Jakob syndrome and an immunological rejection. If the human amnion is sufficiently crosslinked, for example, by glutaraldehyde to decrease these medical risks and to improve the properties of material, the modified human amnion cannot be absorbed in the body, and as a result, a foreign substance is present in the body such as the case of TEFLON™ (polytetrafluoroethylene). Thus, chemically modified materials are disadvantageous in that the materials permanently remain in the body and are further encapsulated by surrounding tissue, and the encapsulated tissue portion is thickened and enlarged with the elapse of time. Consequently, disadvantageous disorders, such as adhesion between the peripheral tissues are caused. In this way, the above-mentioned conventional medical devices are not medical devices for homologous transplantation.

A medical prosthesis made of a human cerebral dura mater, which has cell tissues, has been used for several decades, and is accepted as a medical prosthesis for homologous transplantation. However, it is not legally accepted to be applied to a biological region except for the human cerebral dura mater. Moreover, it has been recently reported that a serious side effect, that is epilepsy, occurs after the prosthesis on human cerebral dura mater. Furthermore, since the medical prosthesis made of a human cerebral dura mater is collected from a human body, the material is disadvantageous in its poor ability of supply and extremely high cost. Thus, the medical prosthesis made of a human cerebral dura mater has a critical defect that it is not equally offered in terms of medical welfare.

When a defective part undergoes anaplerosis or prosthesis by exsection in an abdominal organ, it is impossible to suture the defective part as it is in the case where the organ is a feeble organ such as the liver. On the other hand, when a defective part undergoes anaplerosis or prosthesis by exsection in a bone, significant strength is required to suture and fix the defective portion. In such a case, a suture reinforcing material excellent in strength and flexibility is required.

Thus, a medical device, which is excellent in strength, softness and flexibility and has bioabsorption ability, is required. For example, a mesh fabric made of polyglycolic acid is used as a medical device satisfying the above conditions. However, since the mesh fabric is permeable, it disadvantageously leaks body fluid, for example, bile from a gallbladder, from an organ to which the mesh fabric is applied.

In prosthetic therapy of an affected portion, a medical device is required to satisfy the following conditions: capability of preventing liquid and gas in the applied portion from being leaked and lost; easiness to be sutured; capability of reinforcing by suture; bioabsorption to promote regeneration and self-repair of tissue of an affected part; excellent biocompatibility; excellent operativeness, for example, easiness to treat in surgical operations in terms of adhesion to a defective part; stably supply at reasonable cost.

SUMMARY OF THE INVENTION

The medical device of the present invention consists essentially of stratum compactum of tissue membrane.

In one embodiment of the present invention, the tissue membrane is human amnion.

In another embodiment of the present invention, a matrix pattern on a top face of the stratum compactum is asymmetrical with respect to a matrix pattern on a bottom face thereof.

In still another embodiment of the present invention, the medical device is membranous.

In still another embodiment of the present invention, the medical device is fibrous.

In still another embodiment of the present invention, the medical device is tubular.

According to one aspect of the present invention, the composite medical device of the present invention comprises a medical material consisting essentially of stratum compactum of tissue membrane and a bioabsorbable material.

In one embodiment of the present invention, the bioabsorbable material is polyglycolic acid, polylactic acid, or a copolymer including glycolic acid or lactic acid as main components.

In another embodiment of the present invention, the bioabsorbable material is a mesh-like material having an average diameter of a pore in the range of about 100 to about 2000 $\mu$m.

In still another embodiment of the present invention, the medical material is membranous and the bioabsorbable material is flat sheet-shaped, and the composite medical device has a sandwich-like structure in which the bioabsorbable material is interposed between a pair of membranous medical materials.

In still another embodiment of the present invention, the medical material is membranous, and the medical material is reinforced with stitching of a fibrous material made of the bioabsorbable material.

According to another aspect of the present invention, a method for producing a medical device consisting essentially of stratum compactum of tissue membrane, includes the steps of: separating tissue membrane including stratum compactum from tissue; sterilizing or disinfecting the separated tissue membrane; and removing all other layers except the stratum compactum from the sterilized or disinfected tissue membrane using an enzyme.

Thus, the invention described herein makes possible the advantages of: (1) providing a medical device excellent in bioaffinity and biocompatibility; (2) providing a medical device capable of effectively completing regeneration and self-repair of tissue of a defective portion, which is an effective substitute for the defective portion along with regeneration of tissue of the defective portion and then is degraded to be absorbed in a human body or to be excreted so as not to remain in the body; (3) providing a medical device excellent in operativeness in surgical operations, which provides simplified operations and reduced operation time by enabling both manual and instrumental suture and anastomosis and obviating drainage; (4) providing a composite medical device, which is obtained by effectively reinforcing a medical device having the above excellent effects, useful for anaplerosis and prosthesis of an affected site and repairing a defective site; (5) providing a method for producing a medical device having the above-mentioned excellent effects; and (6) providing a medical device and a composite medical device providing pharmaceutical economic efficiency capable of reducing the medical expense by facilitating the treatment of a defective part, reducing hospitalization and rehabilitation time periods of a patient, reducing a time period required for a surgical operation and simplifying surgical operations.

These and other advantages of the present invention will become apparent to those skilled in the art upon reading and understanding the following detailed description with reference to the accompanying figures.

DESCRIPTION OF THE PREFERRED EMBODIMENTS

Figure 1:
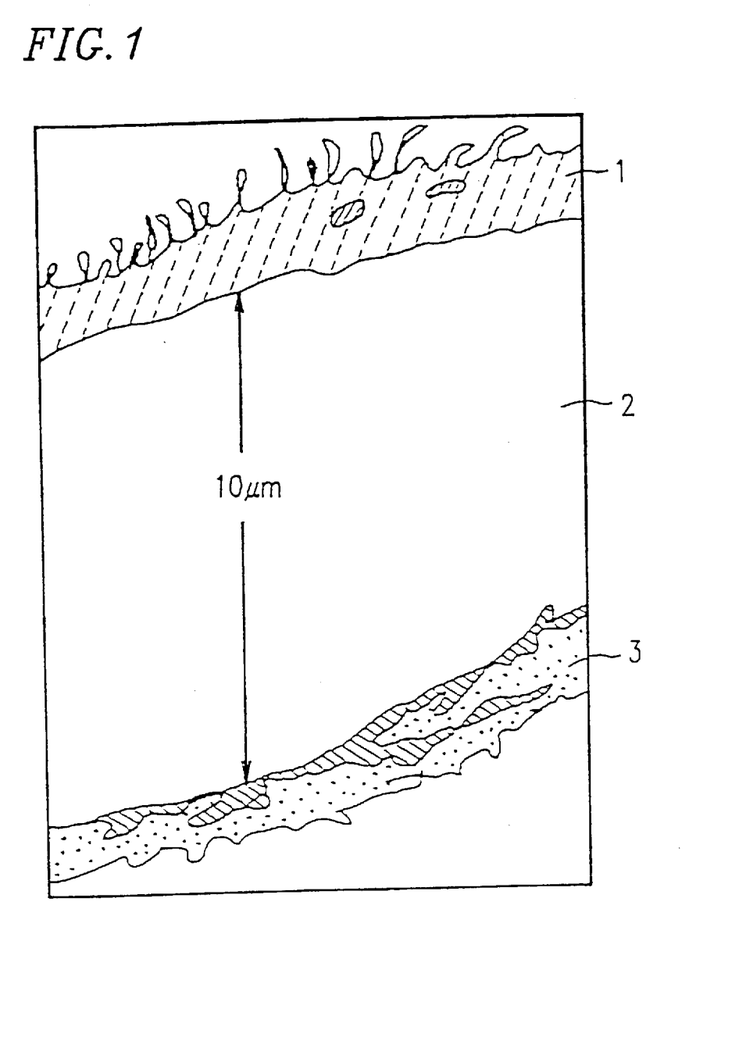
FIG. 1 is a cross-sectional view showing the constitution of human amnion.

A medical device according to the present invention consists essentially of stratum compactum of tissue membrane, more specifically, stratum compactum of connective tissue membrane. In the present invention, the wording "consists essentially of stratum compactum" means that a medical device only includes the stratum compactum but does not include any other components of the tissue membrane such as epithelium, basement membrane and fibroblast. The medical device may, however, include these other components at such an extremely small amount that these components remain only as a trace. The stratum compactum has acellular nature. The stratum compactum of the tissue membrane comprises a collagen layer including type I, type III, type IV, type V and type XVI collagens, in which collagen fibers are present in a finely reticulate form. The medical device according to the present invention is obtained by removing tissue membrane containing stratum compactum from body tissue and further removing the stratum compactum therefrom. The tissue membrane includes human cerebral dura mater, human fascia lata, horse pericardium, pig pericardium and human amnion. Preferably, a medical device according to the present invention is made of human amnion. FIG. 1 is a cross-sectional view showing the constitution of human amnion (NANKODO Corporation Limited; KISO TO RINSYO (Basic Medicine and Clinical Medicine), 1981, "Placenta", See page 31, FIG. 34 for amnion at the 13th week of pregnancy)

With reference to FIG. 1, the human amnion comprises: epithelium and basement membrane 1 (both collectively denoted by the reference numeral 1); stratum compactum 2 having a width of about 10 μm; and fibroblast 3. A medical device according to the present invention consists essentially of stratum compactum 2, excluding epithelium, basement membrane 1 and fibroblast 3 from human amnion. As described later, the components except for stratum compactum 2 are essentially eliminated by conducting the following treatments on human amnion. A method for obtaining a medical device, in particular, a membranous medical device, according to the present invention will be described in detail below taking human amnion as an example.

First, a fetal membrane alone is removed and separated from fresh placenta, umbilical cord and the like of an uninfected woman in the state of maternity immediately after parturition. Blood is immediately removed from the separated fetal membrane by washing with a physiological saline solution defined by the Japanese Pharmacopoeia No. C-1365, i.e., an isotonic sodium chloride solution.

The fetal membrane from which blood is removed is desalinizated and washed with aseptic non-pyrogenic purified water. The desalinizated and washed fetal membrane is allowed to stand in 0.1% benzalkonium chloride solution defined by Japanese Pharmacopoeia No. C-370 for 24 hours or more. It is considered that a treatment in the benzalkonium chloride solution described above causes separation among membrane layers constituting the fetal membrane such as amnion, chorionic membrane, decidua capsularis and decidua basalis, disinfection and sterilization, and denaturalization of the cell-containing layers.

The amnion separated by such a treatment is subjected to ultrasonication using aseptic non-pyrogenic purified water.

Next, the thus obtained amnion is subjected to enzymatic treatment. The enzyme includes ficin which is one of a number of thiol proteases. The amnion is immersed in 0.2M phosphate buffer solution, pH of about 7.0 to about 7.5, preferably, pH of about 7.4, containing 0.01% ficin at room temperature for 24 hours. Subsequently, the amnion treated with ficin is subjected to ultrasonic washing using aseptic non-pyrogenic purified water.

The thus obtained membranous material substantially only includes stratum compactum, and excludes all components except for stratum compactum from amnion. This is confirmed by the following features of the resultant membranous material.

(1) No cell-containing layer is found in the membranous material through microscopic observation. Moreover, a matrix structure in which a pattern on a surface is asymmetrical with respect to a matrix pattern on a bottom face, which is assumed to be possessed by stratum compactum included in human amnion, is observed.

(2) A ratio of the thickness of stratum compactum to the total thickness of human amnion is in the range of about 70 to about 80%. In the case where a thickness of the membranous material, obtained by the above-mentioned treatment, is measured for 30 times, and the calculated average ratio of the thickness is 77%.

(3) The membranous material is acellular and is composed of collagens, which include collagens of type I, type III, type IV, type V and type XVI (*J. Biochem.* 112, 856–863 (1992)).

The above-mentioned membranous material may be further subjected to sterilization, disinfection, crosslinking and modification.

The sterilization or disinfection treatment includes heating including a treatment using an autoclave, UV irradiation, electron beam irradiation, gamma irradiation and a treatment with ethylene oxide gas.

The crosslinking or modification includes a process of a crosslinking reaction using glutaraldehyde carbodiimide or succinic anhydride.

Since the above membranous material is strong enough, the membranous material can be used as a medical device without conducting any further treatments or processes. The membranous medical device can be used as a medical product such as a donor-site skin graft, and wound and burn dressings. The membranous medical device is also used as a medical prosthesis for a defective part of a pleura in combination with fibrin coagulation. Safety and effectiveness of the membranous medical device as a homograft allowing the regeneration and self-repair of tissue can be demonstrated through animal experiments.

In one embodiment, the medical device according to the invention can be fibrous. The fibrous material includes filaments, threads and the like. For example, the threads can be obtained by cutting the membranous material or the membranous material immersed into gelatine or collagen solution into strips and twisting the strips into threads. Furthermore, a plied thread can be formed by plying and twisting the obtained threads. This fibrous material is physically crosslinked, i.e., entangled, or chemically crosslinked to form an extremely strong thread or plied thread. The resultant fibrous medical devices can be used as medical devices for homologous transplantation.

In another embodiment, the membranous material may be formed into a tubular member. The tubular member can be formed by, for example, a filament winding method. The filament winding method includes the steps of: winding the thread or the piled thread prior to being crosslinked around a bar-shaped core material in a layered manner in a wet state so as not to leave any space; crosslinking the wound material by the addition of a crosslinking agent, resulting in a tubular material; and removing the bar-shaped core material therefrom. A strip material obtained by cutting the membranous material produced by the above method into a strip also can be used as a starting material instead of the thread in the filament winding method. The tubular medical device may be used for an artificial urethra, an artificial ureter, an artificial esophagus, an artificial trachea or an artificial blood vessel used for homologous transplantation.

In the case where a membranous medical device is used for prosthesis of a portion of an abdominal organ to be subjected to an operation, the strength of the membranous device merely made of stratum compactum may be insufficient for performing prosthesis. Therefore, the membranous material made of stratum compactum may be reinforced with a reinforcing material so as to be used as a composite medical device.

The reinforcing material used in the present invention is a bioabsorbable material. The bioabsorbable materials can be either naturally-occurring or synthetic. In a preferred embodiment, the bioabsorbable material is polyglycolic acid, polylactic acid or a copolymer including components thereof (i.e., glycolic acid and/or lactic acid) as main components.

Although the reinforcing material can be a cloth including a textile and a knitting fabric, a fibrous material or a mesh-like material, the form of the reinforcing material is not particularly limited. In one preferred embodiment of the invention, the reinforcing material is a mesh-like material having an average pore diameter in the range of about 100 to about 2000 μm.

Figure 2:
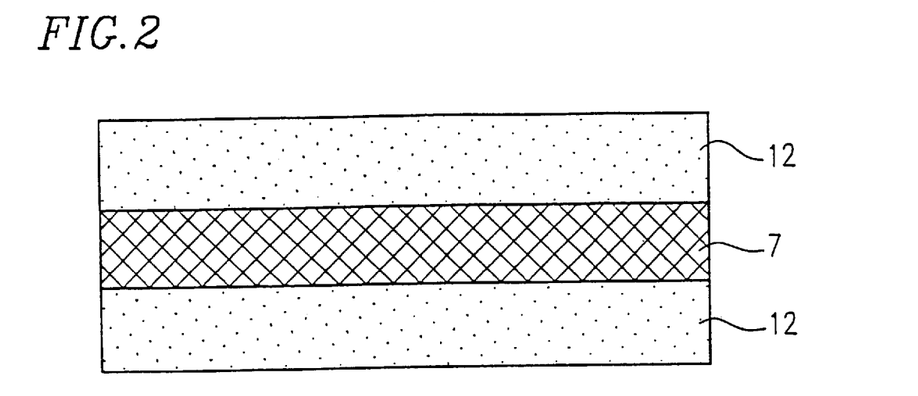
FIG. 2 is a cross-sectional view showing an example of the structure of a composite medical device according to the present invention, which consists of a three-layered material containing a reinforcing membrane.

As an example of a composite medical device according to the present invention, a sandwich-like layered structure is shown in FIG. 2. The composite medical device has a sandwich-like structure in which a bioabsorbable material 7 is interposed between a pair of membranous medical materials 12 each consisting essentially of stratum compactum. Preferably, the composite medical device according to the present invention has such a structure that a mesh-like bioabsorbable material is interposed between a pair of membranous materials made of stratum compactum of human amnion. Any method may be used as a method for laminating the membranous medical materials 12 each made of stratum compactum and the membranous bioabsorbable material 7. For example, roller compression can be used.

The above-mentioned sandwich-like layered structure is produced, for example, as follows. First, a pair of membranous materials immersed into gelatine or collagen solution and a mesh fabric made of polyglycolic acid immersed into gelatine or collagen solution interposed therebetween. Then, gelatine or collagen molecules which are uniformly dispersed through the three membranous materials are chemically crosslinked or physically crosslinked, i.e., entangled, resulting in a sandwich-like layered structure integrally formed by crosslinked gelatine or collagen.

In another preferred embodiment, the membranous medical material is reinforced by stitching the membrane made of stratum compactum with a fibrous material made of the bioabsorbable material.

A particularly preferred fibrous material made of the bioabsorbable material is a fibrous material made of polyglycolic acid, polylactic acid or a copolymer including components thereof (i.e., glycolic acid and/or lactic acid) as main components. A twisted thread which is obtained by twisting a strip formed by cutting the membrane made of stratum compactum, preferably, stratum compactum of human amnion and a plied thread which is formed by plying and twisting the twisted threads can also be used.

Figure 3:
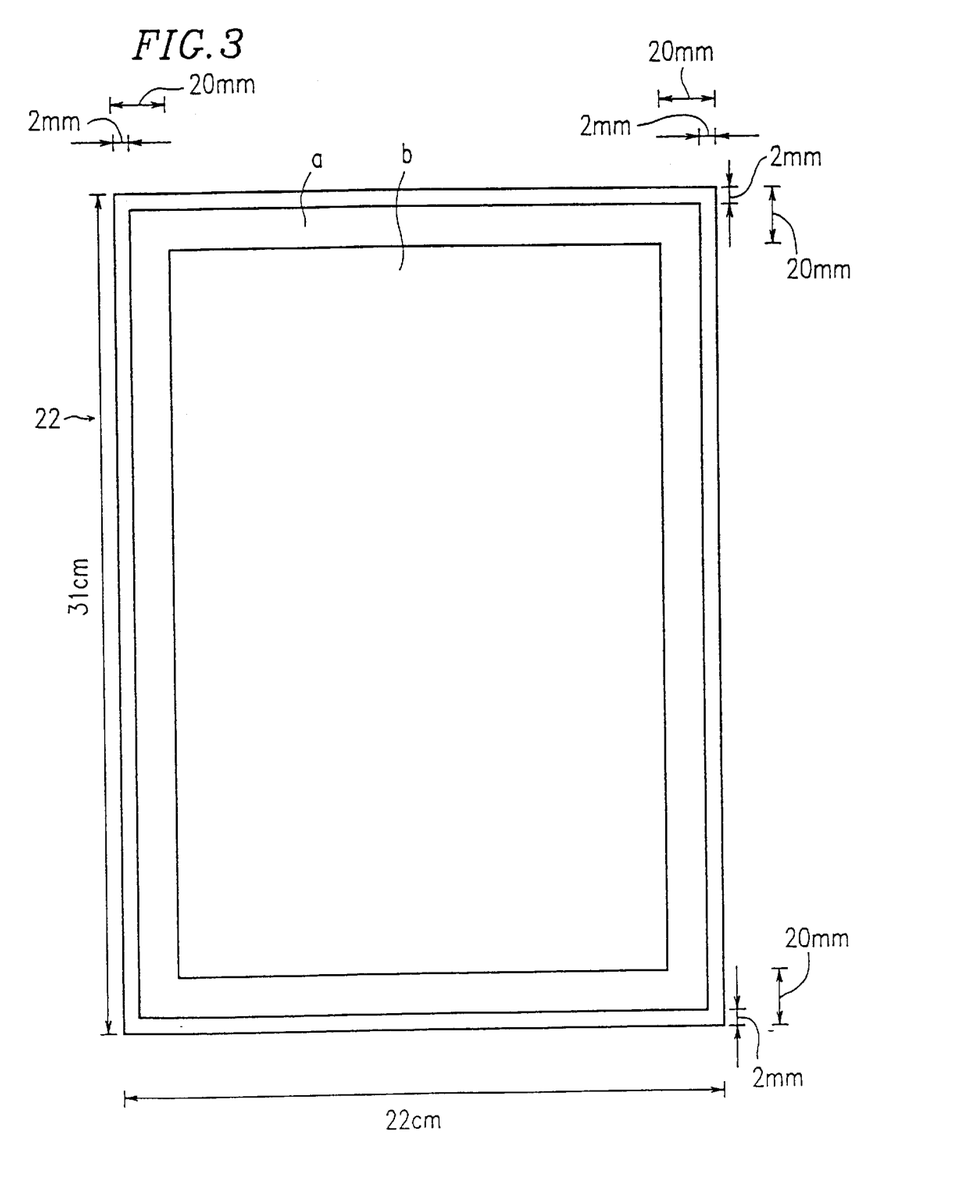
FIG. 3 is a plane view showing an example of a composite medical device according to the present invention, which is reinforced by stitching.

The stitch patterns used herein include, but are not limited to, running stitch and zig-zag stitch. A region where the membranous medical devices is to be reinforced by stitching is not limited. A stitching process can be performed in a peripheral area of the membranous medical device or the entire membranous medical device. FIG. 3 is a plane view showing an example of a composite medical device according to the present invention.

Figure 4:
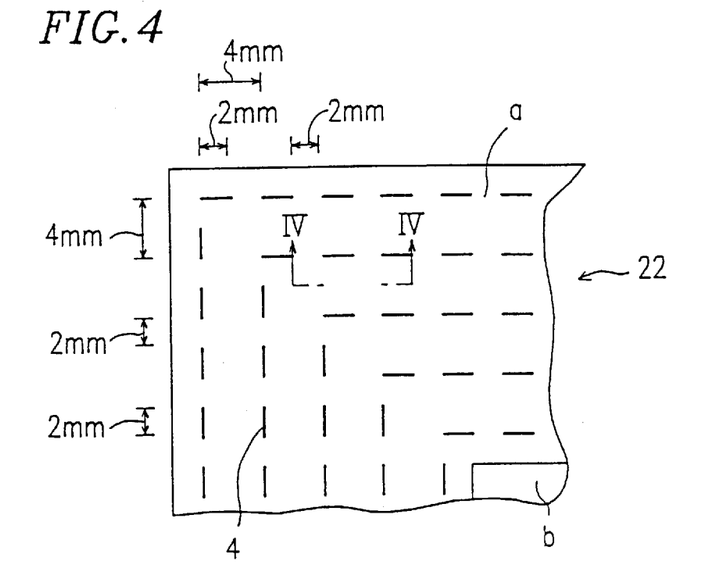
FIG. 4 is an enlarged partial plane view showing a stitch pattern of a peripheral area a shown in FIG. 3.
Figure 6:
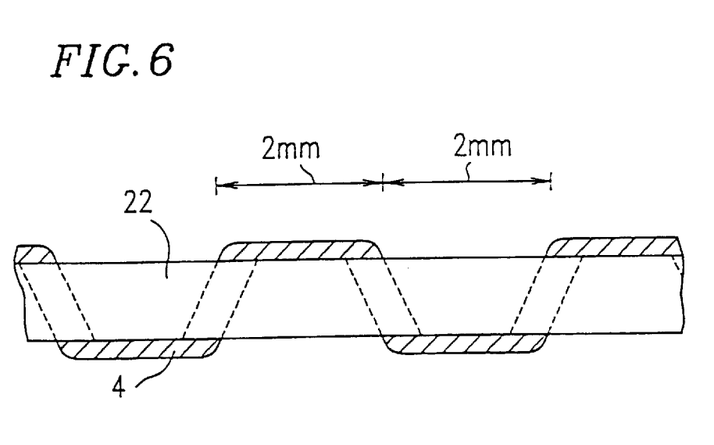
FIG. 6 is a cross-sectional view taken along a line IV—IV in FIG. 4.

A peripheral area a of the composite medical device shown in FIG. 3 is stitched in running stitches, for example, along four sides of the composite medical device. The peripheral area a corresponds to a region between a line 2 mm inside and a line 20 mm inside from the outer circumference of four sides of the membranous material 22. FIG. 4 is an enlarged partial plane view showing the stitch pattern in the peripheral area a. As shown in FIGS. 4 and 6, stitches are done so that an interval between one stitch line and another stitch line is 4 mm and an interval between adjacent stitches is 2 mm. FIG. 6 is a cross-sectional view taken along a line IV—IV in FIG. 4.

Figure 5:
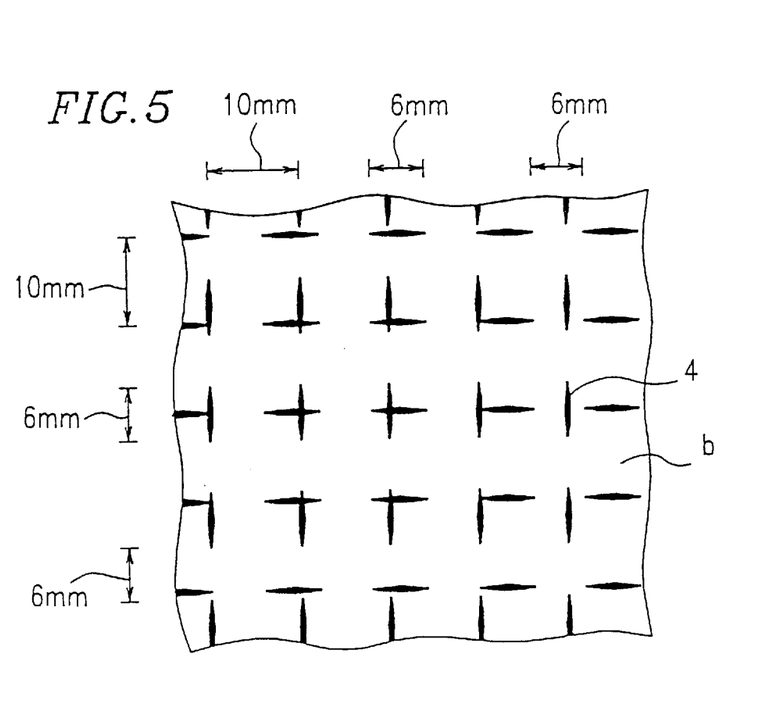
FIG. 5 is an enlarged partial plane view showing a stitch pattern of a central area b shown in FIG. 3.

A central area b surrounded by the peripheral area a can be stitched in running stitches both in vertical and horizontal directions. FIG. 5 shows an enlarged partial plane view showing the stitch pattern in the central area b. As shown in FIG. 5, both in vertical and horizontal directions, stitches are done so that an interval between one stitch line and another stitch line is 10 mm and an interval between adjacent stitches is 6 mm.

The composite medical device reinforced by stitching is excellent in biocompatibility, bioaffinity, strength and flexibility as well as easiness to treat and strength for suture. If a membranous medical material is reinforced by other membranous reinforcing materials, a complicated process is required to tightly join the reinforcing material and the medical material together. Even when the reinforcing material and the medical material are successfully joined together, the reinforced medical device becomes unnecessarily thick. On the other hand, the composite medical device reinforced by being stitched according to certain embodiments of the present invention is scarcely thickened. Thus, the resultant composite medical device is excellent in flexibility allowing the medical device to correspond to any shape, and therefore is excellent in easiness to treat.

The medical device according to the present invention consists essentially of stratum compactum of tissue membrane. In general, tissue is formed by cell growth utilizing stratum compactum as a substrate. According to the present invention, the medical device is used while keeping a matrix of the stratum compactum of the tissue membrane as it is. Therefore, the medical device allows the regeneration, growth and self-repair of defective tissue.

Furthermore, the medical device according to the present invention is excellent in strength and easiness to treat, and therefore is excellent in operativeness in surgical operations. Thus, it is possible to facilitate the treatment in a patient and to allow the patient to leave hospital earlier than usual. The medical device according to the present invention is suitably used for a medical prosthesis and an artificial tissue which are implantable and tissue-regenerative, such as a pledget, a bolster, a patch graft, a suture, a donor-site skin graft, a post-operative antiadhesive, an artificial blood vessel, an artificial urethra, an artificial ureter, an artificial esophagus, an artificial trachea, an artificial membrana tympani, and an artificial oral mucosa. The present invention provides the excellent medical device as described above, thereby facilitating the treatment.

In addition, the human amnion has been treated as medical waste after parturition, and no use of the human amnion has been found. Therefore, it is possible to recover the human amnion as a post-delivery waste. In this way, a large amount of raw material is available at low cost.

The composite medical device according to the present invention can have appropriate flexibility which is almost equal to that of a material before being reinforced. Therefore, the composite medical device is excellent in easiness to treat for prosthesis and anaplerosis of a defective part of the body. The composite medical device not only sufficiently satisfies the requirements such as biocompatibility, bioaffinity, strength and flexibility but also has strength for suture. The resultant composite medical device has remarkable effects on repair of an excised or incised site of an organ such as the liver, pancreas, spleen or gallbladder and prosthesis of a sutured site of bronchus as a medical prosthesis for homologous transplantation having suture reinforcing ability.

Although the present invention will be described below by way of examples, the present invention is not limited thereto.

EXAMPLES (1) Working conditions

A. Working environment

1. Working place

All steps except for ultrasonication are conducted on a clean bench placed in a sterilized room (Class 100).

2. Clothing of an operator

An operator puts on sterilized cap, mask, dust-free garments and shoes in another room before entering the clean room.

All operations are conducted while the operator wears a pair of sterilized disposable rubber gloves. Whenever the operator enters and goes out from the clean room or the operator touches an unsterilized substance, the rubber gloves should be substituted by another pair of sterilized rubber gloves.

B. Water to be used for production and the like

1. Water used for production is always treated according to the following procedure.

Water is filtrated using a prefilter and an ultrafiltration membrane. The filtrated water is periodically collected, and then is subjected to limulus lysate test to detect endotoxin. The water, from which no endotoxin is detected, is used for production.

2. The apparatus should be sufficiently sterilized with 75% ethanol to prevent bacteria growth therein when not used for a long time.

3. Containers and tools used in each step are sufficiently sterilized with 75% ethanol and preserved until their use by immersing into 0.1% benzalkonium chloride solution.

(2) A production method using amnion of human fetal membrane

The membranous medical device was produced according to the following procedures.

An intermediate membrane obtained by each step was preserved in 0.1% benzalkonium chloride solution.

1. Separation of amnion from fetal membrane

A container made of stainless steel is filled with 0.1% benzalkonium chloride solution. Then, a human fetal membrane is placed within the container. The human fetal membrane is bathed in the solution with hands wearing rubber gloves so as to peal off amnion. The obtained amnion is sufficiently washed with water, thereby obtaining a first intermediate membrane.

2. Removal of foreign substances (1)

The first intermediate membrane is spread over a plastic plate so as to remove any milky white casein-like substances. Then, the membrane is sufficiently washed with water, thereby obtaining a second intermediate membrane.

3. Ficin treatment

First, 0.2M phosphate buffer solution, pH 7 is prepared using sodium hydrogenphosphite and sodium phosphite. Then, sodium chloride is added to the buffer solution so as to be 0.9 v/w %, thereby obtaining a buffer solution used in Examples of the present invention.

Next, 5 liter of the buffer solution is poured into a container made of stainless steel. Then, the container is sealed so that the buffer solution is sterilized at 120° C. for 30 minutes. After cooling the buffer solution, 2.5 g of sodium azide is dissolved into the buffer solution. Then, 0.5 g of ficin is dissolved into the obtained solution. Ten second intermediate membranes are put into the container, and are allowed to stand at room temperature for 24 hours. Thereafter, the intermediate membranes are sufficiently washed with water, thereby obtaining third intermediate membranes.

It is preferred that Step 3 is conducted within 24 hours, preferably, several hours, more preferably, one hour after completion of Step 1.

4. Removal of foreign substances (2)

The third intermediate membrane is spread over a plastic plate so as to remove any milky white casein-like substances by rubbing the surface with a plastic strip. Then, the membrane is sufficiently washed with water, thereby obtaining a fourth intermediate membrane.

It is preferred that Step 4 is conducted within 24 hours, preferably, several hours, more preferably, one hour after completion of Step 3.

5. Attachment of frames

A rectangular frame made of polypropylene having an inner dimension of 24 cm long by 33 cm broad is placed on a plastic plate. The fourth intermediate membrane is spread over the frame, and another frame made of polypropylene having the same dimension is superimposed thereon. Then, the two frames and the fourth intermediate membrane are fixed with clips.

6. Ultrasonication

The fourth intermediate membrane fixed with the clips is suspended in a vessel made of stainless steel. The fourth intermediate membrane is subjected to ultrasonication for 15 minutes using a ultrasonic generator while overflowing water.

7. Packing

The membrane obtained by the above steps is impregnated with 0.1% benzalkonium chloride solution. Then, the membrane is put into a sterilized polyethylene bag which is in turn thermally sealed.

The resultant membrane consists essentially of stratum compactum.

(3) Quality of the obtained stratum compactum membrane.

The thus obtained medical device consisting essentially of stratum compactum has the following qualities.

1. The membrane is transparent or semitransparent.

2. No foreign substance is found to be attached to the membrane through observation using a loupe of 10 magnifications.

3. The membrane was placed into an Erlenmeyer flask, and 100 ml of physiological saline was added thereto. The Erlenmeyer flask was sealed with an cap made of aluminum and was heated at 70° C. for 24 hours. After being cooled, the membrane was removed from the Erlenmeyer flask so that a remaining solution serves as a test solution. The test solution was tested in a pyrogen test No. B-329 according to Japanese Pharmacopoeia. The test solution was evaluated as suitable in the test.

4. The membrane was aseptically picked up from the package, and was partially cut into small pieces with a pair of sterilized scissors under aseptic conditions. Then, 5 g of the pieces of the membrane was put into a test tube containing 140 ml of thioglycolate medium for sterility test. A bacterial limit test was conducted in accordance with sterility test No. B-391 according to Japanese Pharmacopoeia. The membrane was evaluated as suitable in the bacterial limit test.

For a fungus limit test, on the other hand, about 1 g of the pieces of the membrane obtained by the same procedure as mentioned above was put into a 200 ml Erlenmeyer flask containing 40 ml of glucose peptone medium. The fungus limit test was conducted in accordance with sterility test No. B-391 according to Japanese Pharmacopoeia. The membrane was evaluated as suitable in the fungus limit test.

(4) Application of the resultant stratum compactum membrane 4.1

The resultant stratum compactum membrane which is a medical device of the present invention was sealed within a bag, and sterilized by gamma irradiation at 2.5 megarad rayage.

The medical device having the following properties: the membranous medical device can be used as a medical product such as a donor-site skin graft, and wound and burn dressings; the membranous medical device can be used as a medical prosthesis for a defective part of a pleura in combination with fibrin coagulation; and the membranous medical device has safety and effectiveness as a homograft allowing regeneration and self-repair of tissue of an affected part. The usefulness of the membranous medical device in combination with the fibrin coagulation as a medical prosthesis was confirmed through the animal experiment as described below.

The membranous medical device was evaluated using pleuras of female beagle dogs (n=4) as follows. The pleura was cut into a piece measuring 2×2 cm$^2$ using a scalpel under the anesthesia by Nembutal intravenous injection and inhalation of halothane to be peeled off. Then, 500 µl of Liquid B (i.e., a mixture of a calcium chloride solution and powdered thrombin) was added dropwise onto the bleeding defective site with a syringe. Then, a square medical device described above measuring 3×3 cm$^2$, which had been washed with distilled water, air-dried, and then sterilized with ethylene oxide gas, was placed on the defective site. Furthermore, 500 µl of Liquid A (i.e., a mixture of an aprotinin solution and a powdered human fibrinogen containing factor XIII) was added dropwise onto the medical device to proceed fibrin coagulation (Beriplast, Behringwerke AG). After one, five and ten minutes following the application of the medical device onto the defective part, internal pressure of respiratory tract was elevated to cause pulmonary fistula in order to examine the substitution effect of the medical device. As a control, the fibrin coagulation was formed by overlaying Liquid A and Liquid B on the defective site of pleura. The results are shown in Table below.

| Individual Number | Internal pressure at which pulmonary fistula is caused (cmH$_2$O) | | |
| --- | --- | --- | --- |
| | One minute after application | Five minutes after application | Ten minutes after application |
| 1 | 35 | 45 | 55 |
| 2 | 20 | 25 | 60 |
| 3 | 15 | 30 | 35 |
| 4 | 15 | 40 | 45 |
| Mean ± standard deviation | 20 ± 8.7 | 34.0 ± 8.2 | 46.0 ± 5.1 |
| Control | 20 | 30 | 30 |

4.2

The membrane obtained in item 4.1 was cut into strips. The obtained strips were twisted into threads. The threads were plied and twisted into a thread. After being sterilized, these obtained threads can be used as sutures for homologous transplantations.

4.3

A tubular member was formed in accordance with a filament winding method. The membrane obtained in 4.1 was cut into strips. The strip was wound around a Teflon™ bar-shaped core material having an outer diameter of 3 mm in a layered manner in a wet state so as not to leave any space. The wound strip was immersed into 0.2% glutaraldehyde solution for 15 minutes so as to cause a crosslinking reaction, or was dried and heated at 105° C. for 24 hours, resulting in a tubular material made of a crosslinked material. Then, the bar-shaped core was removed therefrom. The obtained tubular material was sterilized, resulting in a tubular medical device.

Another tubular medical device was formed in the same manner as described above using the thread obtained in item 4.2.

The resultant tubular medical devices can be used for an artificial urethra, an artificial ureter, an artificial esophagus, an artificial trachea or an artificial blood vessel for homologous transplantation.

4.4

First, 20 g of purified gelatine defined by Japanese Pharmacopoeia No. D-524 was weighed, and was dissolved into 500 ml of hot water. Water is added so as to obtain 2% gelatine solution. Then, a mesh fabric made of polyglycolic acid having a pore of a diameter of 300 µm was immersed into the 2% gelatine solution, and was pulled up therefrom. Then, the mesh was superimposed on the membrane made of stratum compactum (22 cm wide and 31 cm long) obtained in item 4.1. which was spread over a bench. Another membrane was further superimposed on the mesh fabric. The resulting layered material was pressed by a glass roller so that the three layers were sufficiently adhered to each other with gelatine. The obtained layered material was fixed to a polypropylene frame.

The layered material fixed to the polypropylene frames was suspended within a pressure-reducing, drying and heating apparatus under aseptic conditions. Aseptic dried air at 105° C. was allowed to flow and circulated throughout the apparatus for 24 hours. The obtained layered material was not pealed off even in water. The layered material was crosslinked by immersing it into a solution containing 500 ml of 0.02M borate buffer, pH 9.0 and 100 ml of 5% succinic anhydride solution in acetone at room temperature for 2 hours so as to cause succination. After termination of the reaction, the layered material was sufficiently washed with water and dried. Then, the layered material was subjected to a gamma irradiation at 2.5 megarad rayage. As a result, the reinforced layered medical device was obtained. The structure of the thus obtained composite medical device according to the present invention was shown in FIG. 2. The composite medical device has a sandwich-like structure in which the mesh-like bioabsorbable material 7 for reinforcement is interposed between a pair of membranous medical materials 12 each made of stratum compactum.

The thus obtained composite medical device can exhibit remarkable effects on repair and prosthesis of an excised or incised site of an organ such as liver, pancreas, spleen and gallbladder and a sutured site of a organ of bronchus as a medical prosthesis for homologous transplantation having suture reinforcing ability.

4.5

A solution of collagen at a concentration of 0.15% by weight was prepared using a buffer solution containing urea and creatine hydrochloride. The layered reinforced medical device was obtained by the same method as that in item 4.4 except that the collagen solution was used instead of the purified gelatine solution.

The obtained composite medical device can be used for the same application as that of the composite medical device in item 4.4.

4.6

The membranous material 22 made of stratum compactum was prepared according to the process described in item 4.1. The membranous material 22 was rectangular, which measured 22 cm by 31 cm. The membranous material 22 was stitched as shown in FIGS. 3 through 6 under aseptic conditions. A polyglycol acid thread having a size equivalent to No. 40 count was used as a thread 4.

The peripheral area a of the composite medical device shown in FIG. 3 was stitched in running stitches along four sides of the composite medical device. The peripheral area a corresponds to a region between a line 2 mm inside and a line 20 mm inside from the outer circumference of four sides of the membranous material 22. FIG. 4 is an enlarged partial plane view showing the stitch pattern in the peripheral area a. As shown in FIGS. 4 and 6, stitches were done so that an interval between one stitch line and another stitch line is 4 mm and an interval between adjacent stitches is 2 mm.

FIG. 6 is a cross-sectional view taken along a line IV—IV in FIG. 4.

The central area b (a corresponding to a region inside a line 20 mm inside from the outer circumference of the membranous material 22) was stitched in running stitches both in vertical and horizontal directions. FIG. 5 shows an enlarged partial plane view showing the stitch pattern in the central area b. As shown in FIG. 5, both in vertical and horizontal directions, stitches were done so that an interval between one stitch line and another stitch line was 10 mm and an interval between adjacent stitches was 6 mm.

The resultant stitched membranous material was immersed in 2% purified gelatine solution. Then, the membranous material was pressed by a roller made of stainless steel on a stainless plate so as to reduce unevenness of stitches. After having been sufficiently washed with water, the membranous material was fixed between a pair of polypropylene frames with clips and was aseptically dried at 105° C., resulting in a composite medical device. A thickness of the obtained composite medical device was 16 µm.

4.7

The same procedure described in item 4.6 was repeated except that a zig-zag stitch pattern is used as a stitch pattern instead of the running stitch pattern. A composite medical device having a thickness of 15 µm was obtained.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A method for producing a medical device consisting essentially of stratum compactum of tissue membrane, comprising the steps of:

separating tissue membrane including stratum compactum from tissue;

sterilizing or disinfecting the separated tissue membrane; and removing all other layers except the stratum compactum from the sterilized or disinfected tissue membrane using an enzyme.

2. The method of claim 1, wherein the tissue membrane is human amnion.

3. The method of claim 1, wherein a matrix pattern on a top face of the stratum compactum is asymmetrical with respect to a matrix pattern on a bottom face thereof.

4. The method of claim 1, wherein the medical device is membranous.

5. The method of claim 1, wherein the medical device is fibrous.

6. The method of claim 1, wherein the medical device is tubular.

* * * * *

UNITED STATES PATENT AND TRADEMARK OFFICE
CERTIFICATE OF CORRECTION

PATENT NO. : 5,876,451
DATED : March 2, 1999
INVENTOR(S) : YU et al.

It is certified that errors appear in the above-identified patent and that said Letters Patent is hereby corrected as shown below:

Column 1, line 17: change " -wound" to --wound--.
Column 4, line 67: change "pregnancy)" to --pregnancy--.
Column 6, line 4: change "glutaraldehyde carbodiimide" to --glutaraldehyde, carbodiimide--.
Column 9, line 53: No new paragraph should begin; continue the above paragraph.
Column 11, line 14: No new paragraph should begin; continue the above paragraph.

Signed and Sealed this

Sixth Day of June, 2000

Attest:

Q. TODD DICKINSON

*Attesting Officer*　　　　*Director of Patents and Trademarks*

UNITED STATES PATENT AND TRADEMARK OFFICE
CERTIFICATE OF CORRECTION

PATENT NO. : 5,876,451
DATED : March 2, 1999
INVENTOR(S) : Yui et al.

It is certified that error appears in the above-identified patent and that said Letters Patent is hereby corrected as shown below:

Column 1,
Line 17, change "-wound" to -- wound --.

Column 4,
Line 67, change "pregnancy)" to -- pregnancy --.

Column 6,
Line 4, change "glutaraldehyde carbodiimide" to -- glutaraldehyde, carbodiimide --.

Column 9,
Line 53, no new paragraph should begin; continue the above paragraph.

Column 11,
Line 14, no new paragraph should begin; continue the above paragraph.

This certificate Supersedes Certificate of Correction issued June 6, 2000.

Signed and Sealed this

Sixteenth Day of July, 2002

*Attest:*

*Attesting Officer*

JAMES E. ROGAN
*Director of the United States Patent and Trademark Office*